US008299438B2

(12) United States Patent
Fenchel et al.

(10) Patent No.: US 8,299,438 B2
(45) Date of Patent: Oct. 30, 2012

(54) MODEL BASED ESTIMATION OF A COMPLETE OR PARTIAL POSITRON EMISSION TOMOGRAPHY ATTENUATION MAP USING MAXIMUM LIKELIHOOD EXPECTATION MAXIMIZATION

(75) Inventors: Matthias Fenchel, Erlangen (DE); Ralf Ladebeck, Erlangen (DE); Christian J. Michel, Lenoir City, TN (US); Charles C. Watson, Knoxville, TN (US)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 751 days.

(21) Appl. No.: 12/458,575

(22) Filed: Jul. 16, 2009

(65) Prior Publication Data

US 2011/0015904 A1    Jan. 20, 2011

(51) Int. Cl.
*G06F 17/10* (2006.01)
(52) U.S. Cl. ......... 250/363.09; 250/363.02; 250/363.07; 250/370.08; 600/407; 600/410; 600/424; 600/427; 600/442; 703/2
(58) Field of Classification Search .............. 250/363.09
See application file for complete search history.

(56) References Cited

U.S. PATENT DOCUMENTS

| | | | | |
|---|---|---|---|---|
| 5,672,877 A * | 9/1997 | Liebig et al. | ............. | 250/363.04 |
| 5,903,008 A * | 5/1999 | Li | ............. | 250/363.04 |
| 6,310,968 B1 * | 10/2001 | Hawkins et al. | ............. | 382/131 |
| 6,740,883 B1 * | 5/2004 | Stodilka et al. | .......... | 250/363.04 |
| 6,740,886 B1 * | 5/2004 | Hughes | .......... | 250/393 |
| 6,740,887 B1 * | 5/2004 | Parvin et al. | .......... | 250/393 |
| 7,053,376 B2 * | 5/2006 | Amemiya et al. | ........ | 250/363.04 |
| 7,105,824 B2 * | 9/2006 | Stoddart et al. | .......... | 250/363.04 |
| 7,127,026 B2 * | 10/2006 | Amemiya et al. | ............. | 378/19 |
| 7,348,564 B2 * | 3/2008 | Wollenweber et al. | .. | 250/363.04 |
| 7,355,181 B2 * | 4/2008 | Amemiya et al. | ........ | 250/363.04 |
| 7,534,418 B2 * | 5/2009 | Raffel et al. | ................ | 424/1.81 |
| 7,599,540 B2 * | 10/2009 | Koehler | ................ | 382/130 |
| 7,652,259 B2 * | 1/2010 | Kimchy et al. | .......... | 250/370.08 |
| 7,756,310 B2 * | 7/2010 | Manjeshwar et al. | ........ | 382/128 |
| 7,759,646 B2 * | 7/2010 | Amemiya et al. | ........ | 250/363.04 |
| 7,813,783 B2 * | 10/2010 | Thomas et al. | ................ | 600/407 |
| 7,888,632 B2 * | 2/2011 | Ladebeck et al. | .......... | 250/252.1 |
| 7,970,195 B2 * | 6/2011 | Ziegler et al. | ................ | 382/131 |
| 8,000,773 B2 * | 8/2011 | Rousso et al. | ................ | 600/436 |
| 8,013,307 B2 * | 9/2011 | Ye et al. | .................. | 250/363.04 |
| 8,073,109 B2 * | 12/2011 | Gagnon et al. | ................ | 378/131 |
| 8,108,024 B2 * | 1/2012 | Carlsen et al. | ................ | 600/407 |
| 2006/0237652 A1 * | 10/2006 | Kimchy et al. | .......... | 250/363.02 |

(Continued)

OTHER PUBLICATIONS

Zhou et al., A comparative Study of the Effects of Using Anatomical Priors in PET , 1994, IEEE, 1749-1753.*

(Continued)

*Primary Examiner* — David Porta
*Assistant Examiner* — Djura Malevic
(74) *Attorney, Agent, or Firm* — Harness, Dickey & Pierce, P.L.C.

(57) ABSTRACT

Example embodiments are directed to a method of correcting attenuation in a magnetic resonance (MR) scanner and a positron emission tomography (PET) unit. The method includes acquiring PET sinogram data of an object within a field of view of the PET unit. The method further includes producing an attenuation map based on a maximum likelihood expectation maximization (MLEM) of a parameterized model instance and the PET sinogram data.

25 Claims, 4 Drawing Sheets

U.S. PATENT DOCUMENTS

| | | | |
|---|---|---|---|
| 2008/0069414 A1* | 3/2008 | Manjeshwar et al. | 382/128 |
| 2008/0135769 A1 | 6/2008 | Rosen | |
| 2008/0253640 A1* | 10/2008 | Gagnon et al. | 382/131 |
| 2008/0317194 A1* | 12/2008 | Gagnon et al. | 378/4 |
| 2010/0303319 A1* | 12/2010 | Wang | 382/131 |
| 2011/0123083 A1* | 5/2011 | Ojha et al. | 382/131 |
| 2011/0172517 A1* | 7/2011 | Schmidt | 600/411 |

OTHER PUBLICATIONS

Leahy et al., Incorporation of anatomical MR Data for improved funcitonl imaging with PET, Lecture Notes in Computer Science, 1991, vol. 511/1991, 105-120.*

Andre Salomon et al.: "Iterative Generation of Attenuation Maps in TOF-PET/MR Using Consistency Conditions" RWTH Aachen University, Institute of Imaging & Computer Vision, Aachen, Germany, No. 2013.

T.F. Cootes et al.: "Statistical Models of Appearance for Medical Image Analysis and Computer Vision" Imaging Science and Biomedical Engineering, University of Manchester, UK, 2001.

Johan Nuyts et al.: "Simultaneous Maximum A-Posteriori Reconstruction of Attenuation and Activity Distributions From Emission Sinograms" IEEE Trans Med Imaging, 1999; 18 (5):393-403.

Andrei V. Bronnikov "Reconstruction of Attenuation Map Using Discrete Consistency Conditions" IEEE Transactions on Medical Imaging, vol. 19, No. 5, May 2000.

Fabiana Crepaldi et al.: "Activity and Attenuation Reconstruction for Positron Emission Tomography Using Emission Data Only ia Maximum Likelihood and Iterative Data Refinement" IEEE Transactions on Nuclear Science, vol. 54, No. 1, Feb. 2007.

D. Rueckert et al.: "Automatic Construction of 3D Statistical Deformation Models Using Non-Rigid Registration" Lecture Notes in Computer Science, vol. 2208-Springer Verlag, Berlin, Germany, pp. 77-84.

Matthias Fenchel et al.: "Automatic Labeling of Anatomical Structures in MR Fast View Images Using a Statistical Atlas" Siemens Healthcare Sector, MR Division, Applications & Workflow, Erlangen, Germany.

Axel Martinez-Moller et al.: "Tissue Classification as a Potential Approach for Attenuation Correction in Whole-Body PET/MRI: Evaluation with PET/CT Data" The Journal of Nuclear Medicine, vol. 50, No. 4 Apr. 2009.

* cited by examiner

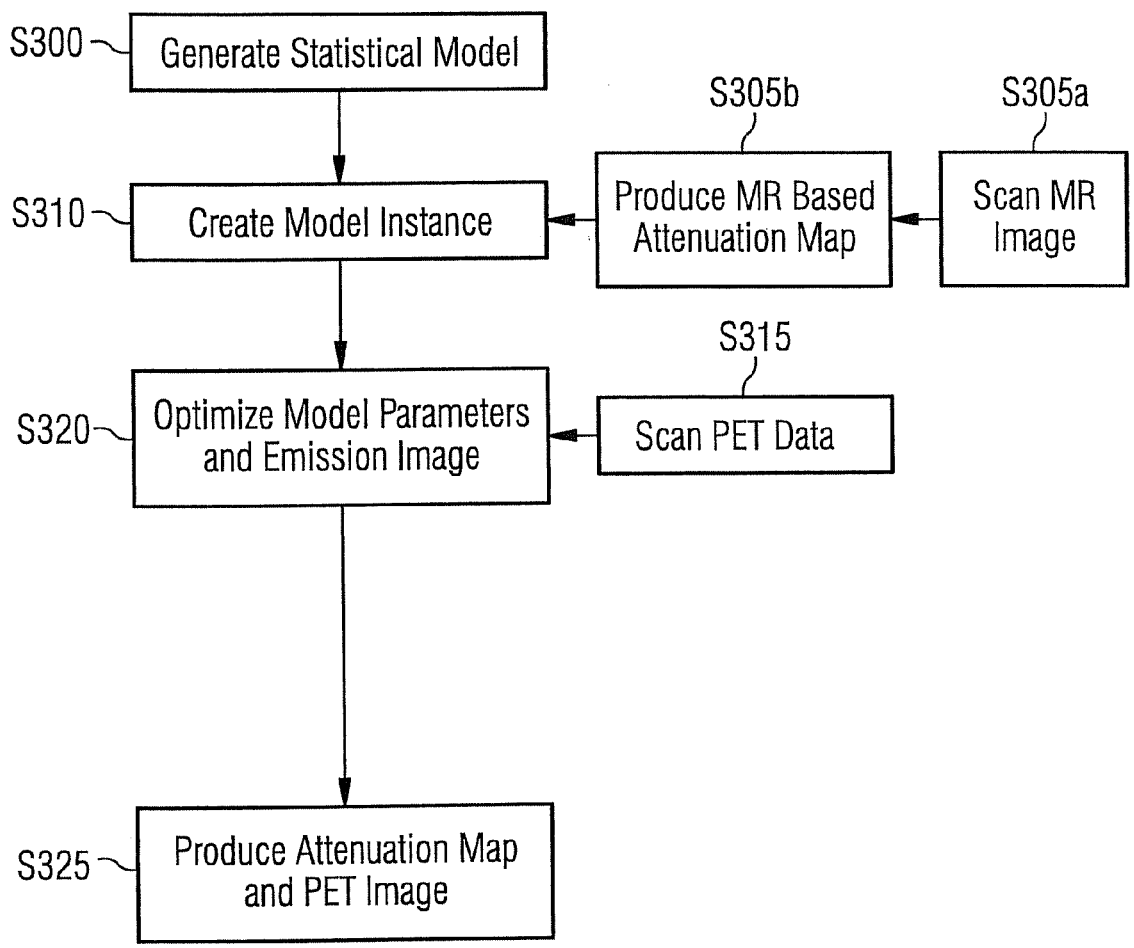

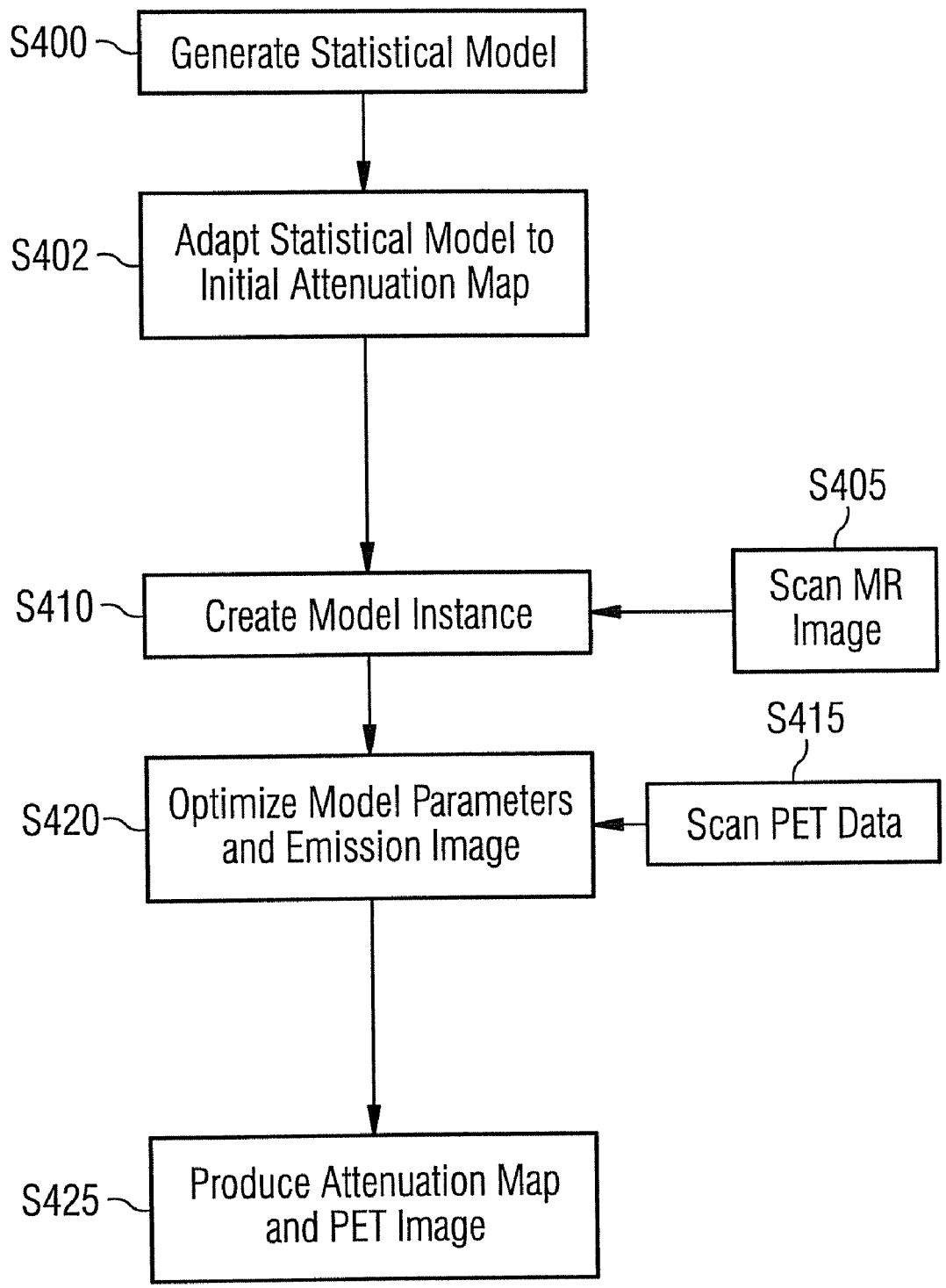

MODEL BASED ESTIMATION OF A COMPLETE OR PARTIAL POSITRON EMISSION TOMOGRAPHY ATTENUATION MAP USING MAXIMUM LIKELIHOOD EXPECTATION MAXIMIZATION

FIELD

Example embodiments relate to methods for estimating an attenuation map in a positron emission tomography and magnetic resonance system (MR-PET).

BACKGROUND

Positron emission tomography (PET) is being used alongside magnetic resonance tomography (MR) in medical diagnostics. While MR is an imaging method for representing structures and slices inside the body, PET allows in vivo visualization and quantification of metabolic activities.

PET uses special properties of positron emitters and positron annihilation in order to quantitatively determine the function of organs and/or cell regions. With this technique, appropriate radiopharmaceuticals marked with radionuclides are administered to the patient prior to the examination. As they decay, the radionuclides emit positrons which after a short distance interact with an electron, causing annihilation to occur. This results in two gamma quanta which fly apart in opposite directions (offset by 180°). The gamma quanta are detected by two opposing PET detector modules within a specific time window (coincidence measurement), as a result of which the annihilation site is localized to a position on the line connecting said two detector modules.

In the case of PET, the detector module generally covers a greater part of a gantry arc length for the purpose of detection. The detector module is subdivided into detector elements having a side length of a few millimeters. On detecting a gamma quantum, each detector element generates an event record that specifies the time and the detection location. This information is passed to a fast logic unit and compared. If two events coincide within a maximum time interval, it is assumed that a gamma decay process is taking place on the connecting line between the two associated detector elements. The PET image is reconstructed using a tomography algorithm, for example, back projection.

In a PET system, such as an MR-PET system, the gamma quanta are attenuated by anything situated between the site of origin of the respective gamma quanta and the PET detector. The attenuation must be taken into account in the reconstruction of PET images in order to prevent image artifacts. Situated between the site of origin of the gamma quantum in the patient's body and the acting PET detector are objects such as tissue within the patient's body, air, and a part of the MR/PET system itself, for example, a patient positioning table. The attenuation values of the objects between the site of origin of the gamma quantum and the acting PET detector are taken into account and compiled into attenuation maps (p maps).

An attenuation map contains attenuation values for each volume element (voxel) of the volume under examination. Thus, for example, an attenuation map can be produced for the patient positioning table. The same applies to, for instance, local coils attached to the patient for MR examinations. In order to produce the attenuation map, the attenuation values are determined and combined. They can be determined by means of, for example, a CT recording or PET transmission measurement of the respective component. Attenuation maps of said kind can be measured on a once-only basis, since the attenuation values do not change over the life of the respective component.

Methods are known by which attenuation values of the patient's body can be determined from anatomical MR images and can be added to the attenuation map. In this case special MR sequences are used by means of which different attenuating tissue classes (e.g., lung tissue), for example, can be identified. With the aid of the MR images it is then possible, based on the position of the attenuating tissue class, to assign appropriate attenuation values to the attenuation map.

However, a transaxial MR field of view is generally smaller than the PET field of view. Therefore, a portion of an object to be examined is only in the PET field of view. Consequently, obtaining attenuation values outside the MR field of view becomes difficult.

MR based estimation of a PET attenuation map may be done either by segmenting the MR image into different tissue types and assigning corresponding attenuation values to the different tissue types. However, this approach does not address the scanned areas outside of the MR field of view.

Recently, maximum-likelihood expectation maximization (MLEM algorithms) has been used to simultaneously reconstruct emission and attenuation maps from PET sinogram data. The PET sinogram data may be referred to as PET raw data, PET counts or PET count data. The term "image" is an image reconstructed from the PET sinogram data. An attenuation map from an MR based segmentation or another known method can be used to initialize the MLEM algorithm.

Other approaches for MR based attenuation correction include the use of an atlas, model or reference image with a known attenuation such as a coregistered corresponding CT, PET transmission image or body contours derived from optical 3D scanning. The actual MR image is then registered to the atlas or reference with known attenuation and the actual attenuation map is deduced from the registration information and additional post-processing methods.

SUMMARY

Example embodiments are directed to model based estimation of a complete or partial PET attenuation map using MLEM.

At least one example embodiment discloses a method of correcting attenuation in a MR scanner and a PET unit. The method includes acquiring PET sinogram data of an object within a field of view of the PET unit and producing an attenuation map based on a maximum likelihood expectation maximization (MLEM) of a parameterized model instance and the PET sinogram data.

At least another example embodiment provides for a method of correcting attenuation in a MR scanner and a PET unit. The method includes acquiring PET sinogram data of an object within a field of view of the PET unit and acquiring MR data of the object within a field of view of the MR scanner. An attenuation map is produced based on a maximum likelihood expectation maximization (MLEM) of a parameterized model instance and the PET sinogram and MR data. The MLEM is constrained by model parameters of the parameterized model instance.

Another example embodiment provides for an apparatus including a positron emission tomography (PET) unit having a plurality of detection units and configured to acquire PET sinogram data of an object within a field of view of the PET unit. A magnetic resonance (MR) scanner is configured to acquire MR data of the object within a field of view of the MR scanner. A computer is configured to produce an attenuation map based on a maximum likelihood expectation maximization (MLEM) of a parameterized model instance and the acquired PET sinogram and MR data, the MLEM being constrained by model parameters of the parameterized model instance.

BRIEF DESCRIPTION OF THE DRAWINGS

Example embodiments will be more clearly understood from the following detailed description taken in conjunction with the accompanying drawings. FIGS. 1-4 represent non-limiting, example embodiments as described herein.

FIG. 1 illustrates a device for superimposed MR and PET image representation that may be used in the example embodiments;

FIG. 2 illustrates a method of estimating a complete PET attenuation map using MLEM to reconstruct a PET image according to an example embodiment;

FIG. 3 illustrates a method of estimating a complete PET attenuation map using an MR based attenuation map and MLEM to reconstruct a PET image according to an example embodiment; and FIG. 4 illustrates a method of refining an initial attenuation map using MLEM according to an example embodiment.

DETAILED DESCRIPTION

Figure 1:
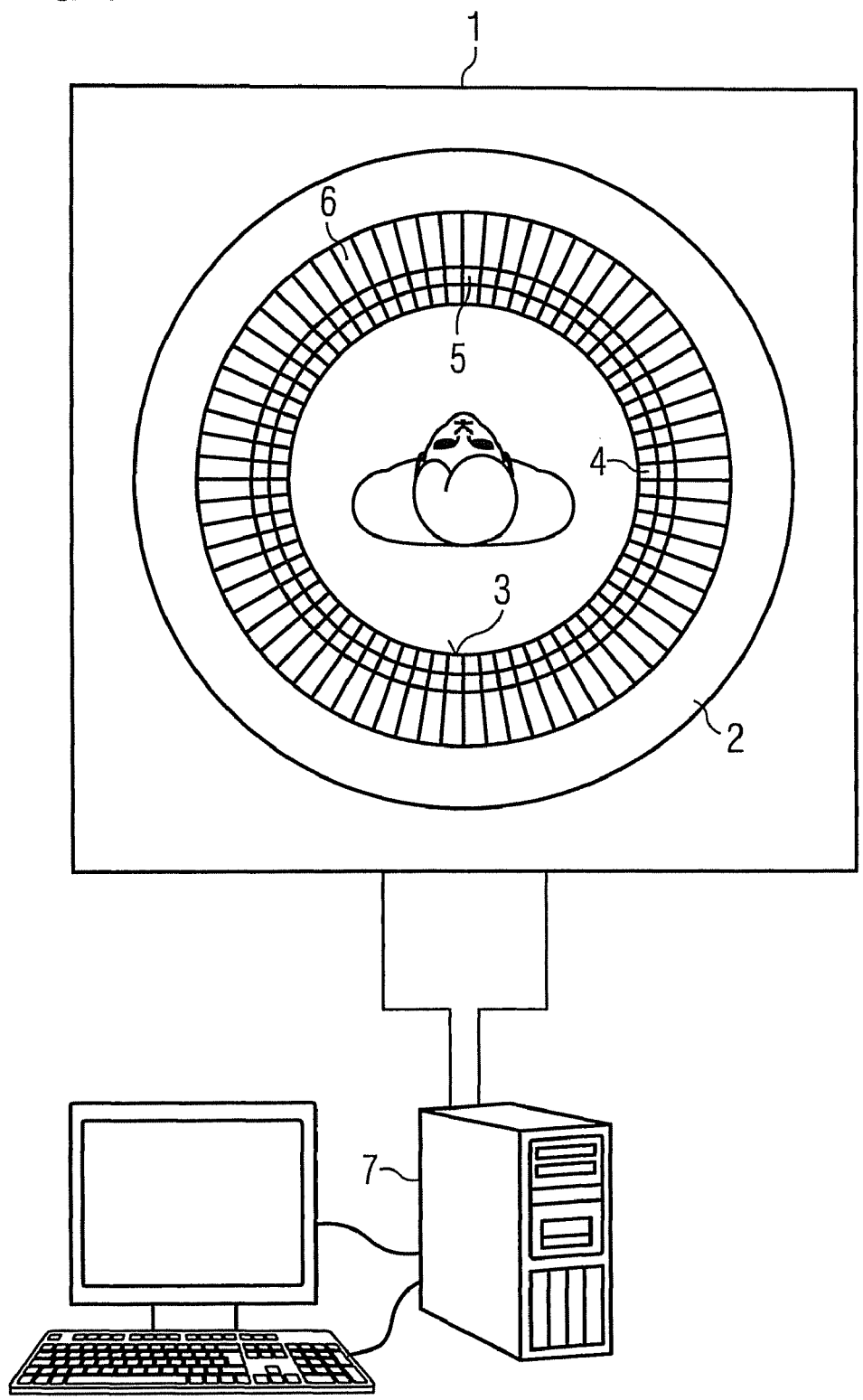

Various example embodiments will now be described more fully with reference to the accompanying drawings in which some example embodiments are illustrated. In the drawings, the thicknesses of layers and regions may be exaggerated for clarity.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, e.g., "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments will be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments are not limited by these aspects of any given implementation.

The term model may mean any kind of attenuation atlas, anatomical attenuation model, attenuation reference image of an object, or any other reference used to estimate a PET attenuation map. Moreover, a deformable model may be implemented which may capture all reasonable shapes of an attenuating object and capture all possible attenuation values at respective spatial positions. The deformable model may vary in shape and appearance.

The term attenuation appearance model of a model refers to the collection of all possible attenuation coefficients at a spatial position within an object such that each spatial position may have a set of potential attenuation coefficients that may occur. An instance of the attenuation appearance model is a specific setting of attenuation coefficients, one for each spatial position of the object.

FIG. 1 shows a device 1 for superimposed MR and PET image representation that may be used in the example embodiments. The device 1 includes a known MR scanner 2. The MR scanner 2 defines a longitudinal direction z that extends orthogonally to the drawing plane of FIG. 1.

As shown in FIG. 1, a PET unit having a plurality of PET detection units 3 arranged in opposing pairs about the longitudinal direction z is disposed coaxially inside the MR scanner 2. The PET detection units 3 include an APD photodiode array 5 preceded by an array of cerium doped lutetium orthosilicate (LSO) crystals 4 and an electrical amplifier circuit (AMP) 6. However, example embodiments are not limited to the PET detection units 3 having the APD photodiode array 5 preceded by an array of LSO crystals 4, but other kinds of photodiodes, crystals and devices can equally be used for detection purposes.

Image processing for superimposed MR and PET image representation is performed by a computer 7.

Along its longitudinal direction z, the MR scanner 2 defines a cylindrical first field of view. The plurality of PET detection units 3 defines, along the longitudinal direction z, a cylindrical second field of view. According to example embodiments, the second field of view of the PET detection units 3 essentially coincides with the first field of view of the MR scanner 2. This is implemented by appropriately adapting the arrangement density of the PET detection units 3 along the longitudinal direction z.

Figure 2:
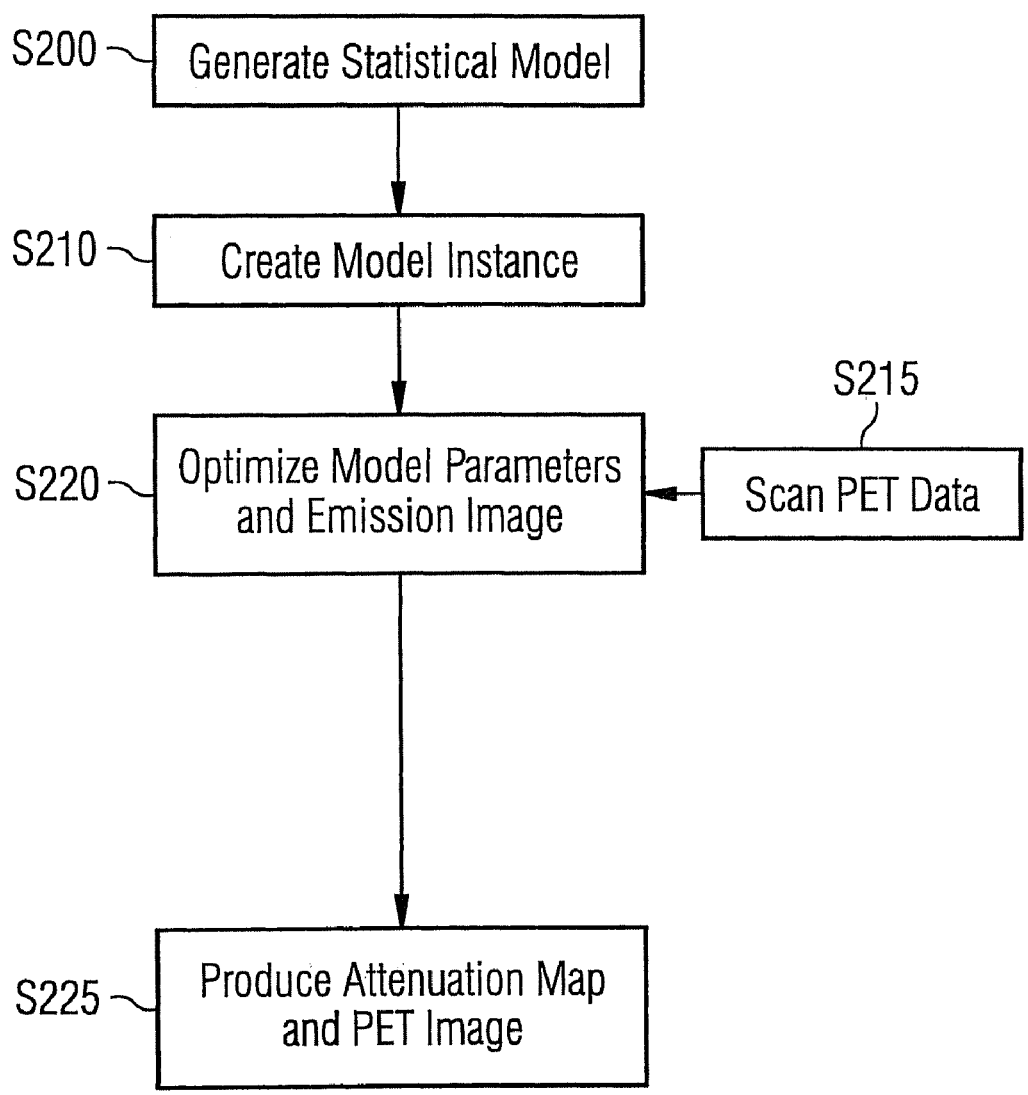

FIG. 2 illustrates a method of estimating a complete PET attenuation map using MLEM to reconstruct a PET image. The MLEM may be any known MLEM. The method of FIG. 2 may be implemented in any PET device or hybrid device with PET modality such as the device 1 illustrated in FIG. 1.

As shown in FIG. 2, a statistical model is generated at S200. While a statistical model is used for illustrative purposes, it should be understood that any other model that may be parameterized may be used in other example embodiments.

The statistical model may be built by performing principal component analysis of deformation fields and attenuation maps resulting from coregistrations of data sets. Data sets may be obtained from scans of multiple individuals and either simple attenuation maps or, corresponding pairs of MR image data and an image from which an attenuation map can be induced (e.g., MR and CT image pairs from each individual). By coregistering data sets, statistical variations of a shape (e.g., an arm) and attenuation values may be captured. Principal component analysis allows for a more compact representation of the parameter space to be developed.

Principal components may be obtained from principal axis transformations of a covariance matrix of input data such as deformation parameters and attenuation parameters. The principal components are the principal Eigen vectors of the covariance matrix of the input data. Transforming the input data to the principal axis produces a compact linear representation of the input data, from which new instances of the model can be generated by linear combinations. Varying linear combination coefficients of the principal components produce other instances of the statistical model.

It should be understood that statistical analysis methods other than principal component analysis, such as clustering analysis, may be used to reduce dimensionality.

The statistical model may be of the complete body or of any arbitrary body part. For example, the statistical model may be a kinematic arm model in combination with an attenuation map of human arms or a statistical atlas and statistical attenuation map of the complete body, for example. The statistical model may be similar to the model described in Rueckert et al. "Automatic Construction of 3D Statistical Deformation Models Using Non-rigid Registration." *Lecture Notes in Computer Science*, vol. 2208 (2001), 77-84 or Fenchel et al. "Automatic Labeling of Anatomical Structures in MR Fast-View Images Using a Statistical Atlas." *Lecture Notes in Computer Science*, vol. 5241 (2008), 576-84, except that these models are based on grey value images instead of attenuation maps.

The statistical model is parameterized by deformation parameters $d_i$ and attenuation appearance parameters $a_i$ for each instance i. The deformation parameters $d_i$ parameterize the shape of the object. The attenuation appearance parameters $a_i$ parameterize the attenuation coefficients at the spatial positions. Examples of attenuation appearance parameters $a_i$ are attenuation values of different tissue types at their respective spatial position at 511 keV, for example, lung tissue attenuation 0.018/cm.

Both the deformation parameters and the attenuation appearance parameters are obtained from the coregistered data sets. The covariance matrix over all input instances is then computed. From covariance matrices of the parameters, principal components are extracted. An instance of the statistical model can then be described by a linear model:

$$\mu = \sum_{i=0} (p_i * w_i) \qquad (1)$$

where μ is the instance of the statistical model, $p_i$ are the principal components and $w_i$ is the coefficient for the i-th principal component in the linear equation. Generally, the coefficients are selected from an interval of three sigma of the principal values. The coefficients $w_i$ may be the deformation parameters $d_i$ for $1 \le i \le m$ and $w_i$ may be the attenuation appearance parameters $a_i$ for $m+1 \le i \le n$.

Therefore, arbitrary instances may be created by assigning different coefficients. While the example embodiment of generating and parameterizing a statistical model is described above, it should be understood that other methods may be used for other models.

Affine parameters $A_i$, including spatial transformation parameters like such as rotation and translation, may be used to arbitrarily align and scale the statistical model in space. Moreover, $A_i$ can be used to setup a matrix M and a translation vector t by which each spatial position may be transformed to:

$$A(x) = M*x + t \quad (2)$$

after deformation, where x is a vector of a spatial position.

It should be understood that the statistical model may be parameterized by other parameters instead of, or, in addition to the deformation parameters, the attenuation appearance parameters and the affine parameters.

Based on the statistical model, a PET attenuation map given by the model instance μ is created at S210 (e.g., an average model). The PET attenuation map given by the model instance μ may be estimated by the computer. More specifically, the attenuation map for the model instance μ may be a function of $d_i$, $a_i$ and $A_i$ and is defined as:

$$\mu(d_i, a_i, A_i) \quad (3)$$

L is a log likelihood of an emission image (emitter distribution) $L(\lambda, \mu)$ where λ is an emission image (the spatial distribution of the positron emission). The emission image λ is based on an initial emitter distribution image that is computed from PET sinogram data, for example, by back projection. The attenuation map given by the model instance μ is a function of the deformation parameters $d_i$ and the attenuation appearance parameters $a_i$ the affine parameters $A_i$, as shown above. Therefore, $$(\lambda, \mu(d_i, a_i, A_i)) = \arg\max (L(\lambda, \mu(d_i, a_i, A_i))) \quad (4)$$

becomes the parameter setting for the maximum likelihood. Furthermore, it should be understood that the emission image λ may also be parameterized by a model, for example, the statistical model. Moreover, it should be understood that other measures may be integrated into an extended likelihood. For example, if a statistical distribution of the model parameters is known or can be approximated, the likelihood of the model instance itself could be integrated into the likelihood measure.

The larger the amount of data sets, the more comprehensive the statistical model will be and thus, the more generalized the statistical model will be. It should be understood that the statistical model is a possible embodiment of a deformable model and that each instance i of the statistical model is a function of the model parameters for that instance. For example, the deformation parameters $d_i$ and the attenuation appearance parameters $a_i$ the affine parameters $A_i$ are model parameters.

PET sinogram data of an object within a field of view of a PET unit is acquired at S215. The PET sonogram data may be acquired by the PET unit shown in FIG. 1. Based on the PET sinogram data, the emission image λ (PET image) is computed simultaneously with the model parameters. Alternatively, the emission image λ and the statistical model may be computed alternatively by first keeping the emission image λ fixed and updating the statistical model, then keeping the statistical model fixed and updating the emission image.

The emission image λ and the model parameters for that instance are optimized at S220 based on the PET sinogram data. The emission image λ and the model parameters for that instance are optimized in an iterative fashion. During optimization, the emission image λ is computed, the statistical model is updated and the emission image λ is recomputed until optimization has been reached. The model parameters may be the deformation parameters $d_i$, the attenuation parameters $a_i$ and the affine parameters $A_i$.

At S220, the PET attenuation map given by the model instance μ and the emission image λ are reconstructed simultaneously based on a MLEM function. The computer shown in FIG. 1 may reconstruct the emission image λ and the PET attenuation map given by the model instance μ. The emission image λ and the PET attenuation map given by the model instance μ may be reconstructed and optimized based on the log-likelihood of the (un-truncated) measured PET emission which is defined as follows:

$$L(\lambda, \mu(d_i, a_i, A_i)) = \sum_{i=0} (y_1 * \log(y_i') - y_1') \quad (5)$$

where $y_i$ is the measured PET sinogram data and $y_i'$ is the estimated $y_i$ value. $y_i'$ is estimated by forward projecting the emission image λ and correcting attenuation by the attenuation map given by the model. L can then be optimized as a function of the parameters $d_i$, $a_i$ and $A_i$ and λ. Here, constraining the MLEM to the parameter space of the model is used to estimate the complete attenuation map. The parameter space means all possible values of the parameterized statistical attenuation model. In the example embodiment shown in FIG. 2, the parameter space may include all model parameters, for example, all deformation, attenuation appearance and affine transformation parameters.

The model parameters are optimized in an iterative fashion until a maximum likelihood has been reached. The optimum can be found by any common optimization algorithm. The optimum is the parameter setting for which the maximum likelihood reaches a maximum value. The optimum defines the most likely instance of the parameterized model for attenuation and emitter image.

When the optimization algorithm at S220 has converged, the optimum maximum likelihood has been reached. The attenuation map is then obtained directly from the model instance and the PET image from the emission image at S225. It should be understood that the emission image obtained at S225 may be discarded when another PET image reconstruction is triggered using the attenuation map.

FIG. 3 illustrates a method of estimating a complete PET attenuation map using an MR based attenuation map and MLEM to reconstruct a PET image according to an example embodiment. The method of FIG. 3 may be implemented in any PET device or hybrid device with PET modality such as the device 1 illustrated in FIG. 1.

As shown in FIG. 3, a statistical model is generated at S300. S300 is the same as S200. Therefore, a detailed description of S300 will be omitted for the sake of clarity and brevity.

At S305a, an object is scanned by an MR unit within the field of view of the MR unit to acquire MR data. The MR scanner shown in FIG. 1 may be used to acquire the MR data.

Once the object is scanned, an MR based attenuation map is produced at S305b. The MR based attenuation map may be generated by any known method of generating an MR based attenuation map and may be produced by the computer shown in FIG. 1.

Based on the MR based attenuation map and the statistical model, a PET attenuation map for a model instance μ is created at S310. S310 is the same as S210, except that the PET attenuation map for the model instance μ is constrained by the MR based attenuation map. Therefore, a detailed description of S310 will be omitted for the sake of clarity and brevity.

PET sinogram data of an object within a field of view of a PET unit is acquired at S315. S315 is the same as S215.

At S320, the model parameters for the instance are optimized. S320 is the same as S220. The model parameters are optimized until a maximum likelihood has been reached.

Once a maximum likelihood of the PET attenuation map for the model instance μ and the emission image λ has been reached, the attenuation map for the model instance μ defines an optimal attenuation map for the model instance μ at S325. The reconstructed PET image is also produced at S325, but may be discarded when the optimal attenuation map for the model instance μ can be used in another reconstruction process to obtain a PET image. Methods of combining MR based attenuation maps and PET attenuation maps are known in the art. Therefore, for the sake of clarity and brevity, they will not be discussed.

FIG. 4 illustrates a method of refining an initial attenuation map using MLEM according to an example embodiment. The method of FIG. 4 may be implemented in any PET device or hybrid device with PET modality such as the device 1 illustrated in FIG. 1. As shown in FIG. 4, at S400, a statistical model is generated in the same manner as in FIGS. 2 and 3.

At S402, the statistical model being parameterized is adapted to an initial attenuation map. The initial attenuation map may be generated beforehand from a low-resolution MR image or a transmission scan, for example. In another example embodiment, a parameterized model that includes anatomy which frequently extends outside a MR field of view (e.g., a kinematic model of the human arms) may be added to the initial attenuation map or may be used to complete the initial attenuation map.

At S405, an object is scanned by an MR unit within the field of view of the MR unit to produce an MR image. At S410, a model instance is created. The model instance is created based on a best fit of the initial attenuation map with respect to a least squares approach. For statistical models, the best fit may be computed by performing an orthogonal projection of the initial attenuation map to the linear space of the statistical model, for example. Thus, the model that is created is an average instance of the statistical model scaled to the initial attenuation map.

At S415, PET sinogram data is scanned and then the model parameters of the attenuation map for the model instance μ are optimized at S420. S415 and S420 are the same as S215 and S220, respectively. Therefore, S415 and S420 will not be described in greater detail, for the sake of clarity and brevity. At S420, the initial attenuation map is refined using MLEM.

At S425, a refined attenuation map is produced based on the maximum likelihood of the attenuation map for the model instance μ. A PET image is also produced.

As described above, the methods may be used for estimating a complete attenuation map of an object based on a model using MLEM reconstruction and/or to complete missing parts of an attenuation map which is computed with other methods before by means of a model. Moreover, the example embodiments may be used for refining an attenuation map such as attenuation maps computed from MR-based attenuation map computation methods including initialization of the model and refinement to the data. The example embodiments aid in avoiding local maxima and generate valid and meaningful instances of a model within its parameter space, atlas or reference image.

Example embodiments being thus described, it will be obvious that the same may be varied in many ways. Such variations are not to be regarded as a departure from the spirit and scope of the example embodiments, and all such modifications as would be obvious to one skilled in the art are intended to be included within the scope of the example embodiments.

What is claimed is:

1. A method of correcting attenuation in a magnetic resonance (MR) scanner and a positron emission tomography (PET) unit, the method comprising:
    acquiring PET sinogram data of an object within a field of view of the PET unit; and
    producing an attenuation map based on a maximum likelihood expectation maximization (MLEM) of a parameterized model instance and the PET sinogram data.

2. The method of claim 1, further comprising:
    acquiring MR data of an object within a field of view of the MR scanner; and
    producing a first attenuation map based on the acquired MR data.

3. The method of claim 2, wherein the producing the attenuation map includes producing the first attenuation map and a second attenuation map.

4. The method of claim 3, wherein the second attenuation map provides maximum likelihood of the PET sinogram data within a field of view of the PET unit including all parts not within the field of view of the MR scanner.

5. The method of claim 1, wherein the producing the attenuation map includes,
    generating a model,
    parameterizing the model by model parameters, and
    creating the parameterized model instance based on the acquired PET sinogram data and the parameterized model.

6. The method of claim 5, wherein the model is a statistical model.

7. The method of claim 6, wherein the parameterizing the statistical model includes parameterizing the statistical model by deformation parameters, attenuation parameters and affine parameters.

8. The method of claim 6, wherein the generating the statistical model includes performing principal component analysis of deformation fields and attenuation maps resulting from coregistrations of example data sets.

9. The method of claim 1, wherein the producing the attenuation map includes,
    generating a model, and
    adapting the model to an initial attenuation map, the parameterized model instance being created based on the adapted model.

10. The method of claim 1, wherein the PET unit is configured to acquire the PET sinogram data.

11. The method of claim 1, wherein a computer connected to the MR scanner and the PET unit is configured to produce the attenuation map.

12. A non-transitory computer-readable medium, when run on a computer, configured to instruct the computer to perform the method of claim 1.

13. A method of correcting attenuation in a magnetic resonance (MR) scanner and a positron emission tomography (PET) unit, the method comprising:

acquiring PET sinogram data of an object within a field of view of the PET unit;

acquiring MR data of the object within a field of view of the MR scanner;

producing an attenuation map based on a maximum likelihood expectation maximization (MLEM) of a parameterized model instance and the acquired PET sinogram and MR data, the MLEM being constrained by model parameters of the parameterized model instance.

14. The method of claim 13, wherein the producing the attenuation map includes producing a PET attenuation map.

15. The method of claim 14, wherein the producing the PET attenuation map includes, generating a model, parameterizing the model by the model parameters, and creating the parameterized model instance based on the parameterized model.

16. The method of claim 15, wherein the model is a statistical model.

17. The method of claim 16, wherein the model parameters are the deformation parameters and the attenuation appearance parameters.

18. The method of claim 17, wherein the model parameters further include affine parameters.

19. The method of claim 14, further comprising:

producing an MR attenuation map.

20. The method of claim 13, wherein the producing the attenuation map includes, generating a model, and adapting the model to an initial attenuation map, the parameterized model instance being created based on the adapted model.

21. The method of claim 13, wherein the PET unit is configured to acquire the PET sinogram data.

22. The method of claim 13, wherein a computer connected to the MR scanner and the PET unit is configured to produce the attenuation map.

23. The method of claim 13, wherein the MR scanner is configured to acquire the MR data.

24. A non-transitory computer-readable medium, when run on a computer, configured to instruct the computer to perform the method of claim 13.

25. A device comprising:

a positron emission tomography (PET) unit including a plurality of detection units and configured to acquire PET sinogram data of an object within a field of view of the PET unit;

a magnetic resonance (MR) scanner configured to acquire MR data of the object within a field of view of the MR scanner; and a computer configured to produce an attenuation map based on a maximum likelihood expectation maximization (MLEM) of a parameterized model instance and the acquired PET sinogram and MR data, the MLEM being constrained by model parameters of the parameterized model instance.

* * * * *